US009488619B2

(12) United States Patent
Nesic et al.

(10) Patent No.: US 9,488,619 B2
(45) Date of Patent: Nov. 8, 2016

(54) DEVICE AND METHOD FOR MONITORING INTERACTION BETWEEN A FLUID AND A WALL

(75) Inventors: Srdjan Nesic, Athens, OH (US); Valery A. Sheverev, West Orange, NJ (US)

(73) Assignee: Ohio University, Athens, OH (US)

( * ) Notice: Subject to any disclaimer, the term of this patent is extended or adjusted under 35 U.S.C. 154(b) by 376 days.

(21) Appl. No.: 14/126,165

(22) PCT Filed: Jun. 20, 2012

(86) PCT No.: PCT/US2012/043309
§ 371 (c)(1),
(2), (4) Date: Dec. 13, 2013

(87) PCT Pub. No.: WO2012/177737
PCT Pub. Date: Dec. 27, 2012

(65) Prior Publication Data
US 2014/0116138 A1    May 1, 2014

Related U.S. Application Data (60) Provisional application No. 61/499,575, filed on Jun. 21, 2011.

(51) Int. Cl.
*G01N 17/00* (2006.01)
*G01N 17/04* (2006.01)
(Continued)

(52) U.S. Cl.
CPC ............ *G01N 29/02* (2013.01); *G01N 17/008* (2013.01); *G01N 17/04* (2013.01); *G01N 2013/0216* (2013.01)

(58) Field of Classification Search
CPC .... G01N 17/008; G01N 29/02; G01N 17/04; G01N 2013/0216

USPC .......................................................... 73/579
See application file for complete search history.

(56) References Cited

U.S. PATENT DOCUMENTS 4,669,310 A    6/1987 Lester
4,872,347 A    10/1989 Okabe et al.
(Continued)

FOREIGN PATENT DOCUMENTS

GB        2292226 A     2/1996
WO        2009109203 A1  9/2009

OTHER PUBLICATIONS

European Patent Office; Search Report and Written Opinion in International Application No. PCT/US2012/043309, mailed Sep. 5, 2012; 3 pp.
(Continued)

*Primary Examiner* — J M Saint Surin
(74) *Attorney, Agent, or Firm* — Wood Herron & Evans LLP (57) ABSTRACT

A sensor device and method for monitoring interaction between a fluid and a wall includes includes a mechanical oscillator, a housing, and mechanical response sensing system. The mechanical oscillator includes a floating member formed from a first material configured to be susceptible to the fluid and a support member formed from a second material resistant to the fluid. The mechanical oscillator is affixed within the housing that is adaptably fastened to the structural component such that the floating member contacts the fluid. The mechanical response sensing system is configured to measure a mechanical characteristic of the combined floating member and the support member. The mechanical characteristic is configured to be indicative of the interaction between the fluid and the wall.

24 Claims, 6 Drawing Sheets

(51) Int. Cl.
  *G01N 29/02* (2006.01)
  *G01N 13/02* (2006.01)

(56) References Cited

U.S. PATENT DOCUMENTS

| | | |
|---|---|---|
| 5,072,388 A | 12/1991 | O'Sullivan et al. |
| 5,092,176 A | 3/1992 | Buttram et al. |
| 5,661,233 A | 8/1997 | Spates et al. |
| 5,734,098 A | 3/1998 | Kraus et al. |
| 5,969,235 A | 10/1999 | Allan |
| 6,693,445 B1 | 2/2004 | Sutton |
| 6,928,877 B2 | 8/2005 | Carlson et al. |
| 6,946,855 B1 | 9/2005 | Hemblade |
| 7,681,449 B2 | 3/2010 | Wolf et al. |
| 7,721,605 B2 | 5/2010 | Wolf et al. |
| 7,770,463 B2 | 8/2010 | Sheverev et al. |
| 7,866,211 B2 | 1/2011 | Brown |
| 8,297,128 B2 * | 10/2012 | Delbos ................. G01J 5/0037 73/756 |
| 8,589,087 B2 * | 11/2013 | Martin ................. G01N 17/02 60/39.091 |
| 2006/0037399 A1 | 2/2006 | Brown |
| 2008/0141780 A1 * | 6/2008 | Wavering ............... G01N 17/04 73/723 |
| 2008/0213874 A1 * | 9/2008 | Mitchell ................. G01F 23/14 435/287.1 |
| 2009/0133505 A1 | 5/2009 | Sheverev et al. |
| 2009/0211335 A1 | 8/2009 | Jovancicevic et al. |
| 2011/0066388 A1 | 3/2011 | Snelling et al. |

OTHER PUBLICATIONS

Chinese Office Action in corresponding Chinese case 201280039660X dated Feb. 25, 2016 (12 pages).
Translation of Chinese Office Action in corresponding Chinese case 201280039660 dated Feb. 25, 2016 (12 pages).
Chinese Office Action (first OA) in corresponding Chinese case 201280039660 dated Jun. 4, 2015 (12 pages).
Translation of Chinese Office Action (1st OA) in corresponding Chinese case 201280039660 dated Jun. 4, 2015 (9 pages).

* cited by examiner

DEVICE AND METHOD FOR MONITORING INTERACTION BETWEEN A FLUID AND A WALL

CROSS-REFERENCE TO RELATED APPLICATIONS

This application claims priority to International Patent Application No. PCT/US2012/043309, filed Jun. 20, 2012, which claims priority to U.S. Provisional Patent Application Ser. No. 61/499,575 filed on Jun. 21, 2011, each of which is incorporated by reference herein in its entirety.

TECHNICAL FIELD

The present disclosure relates generally to the field of sensors, and more particularly, to a device and method for measuring interaction effects between a fluid and a solid wall.

BACKGROUND

In some engineering applications structural components are affected by the fluids with which they are in contact. Examples include chemical process equipment and piping systems, water treatment and distribution systems, and oil and gas pipelines. In many of these applications, it is advantageous to monitor damage accumulation, predict component life, and control fluid properties to minimize damage to system structural components. Damage to structural components from fluids can include corrosion, erosion, scale deposition, oxidation or other chemical effects. Many structural components can be difficult to inspect, can be hidden from observation, can cause health and environmental damage in the event of failure, and/or can be costly to maintain. Advanced sensors are needed to actively monitor the physical effects of fluids in contact with structural components and minimize their effect. For example, such sensors can be used to provide feedback in control systems for the injection of green treatment chemicals and corrosion inhibitors to control corrosion, biological growth, scaling in water treatment, chemical process and boiler systems. Advanced monitoring of harmful physical and chemical effects will result in reduced maintenance costs, increased component service life, and safer operations.

Among various types of systems that employ physical contact between the fluid and the structural component, it is particularly desirable to be able to monitor physical and chemical processes when the fluid flows through a conduit. In such systems, the flow may influence erosion, corrosion and/or scale deposition of the conduit surface, potentially leading to breaches of the conduit by the fluid or to clogging the conduit. Therefore, it is important to be able to measure the metal loss or mass deposition of the conduit surface, especially at conduit bends where the metal loss or deposition rate is greatest. A limited range of measurement technologies are conventionally utilized to determine the rate and type of effects that damage the component. These technologies can be grouped into three general categories: 1) metal loss methods, 2) electrochemical methods, 3) acoustic methods.

Metal loss measurement methods include electrical resistance devices and mass loss coupons. An electrical resistance probe can continuously monitor cumulative corrosion rate of metal elements. Such a probe has a sample element that is exposed to the fluid flow. Physical and chemical interaction between the sample element and the fluid change the thickness and hence the electrical resistance of the sample element. The service life of the resistance probes is directly proportional to the probe thickness while the resolution is inversely proportional to it, with the highest resolution achieved at the expense of sensor life. The more sensitive resistance probes have response times of about 100 hours for corrosion rates of 1 MPY. Resolution is reduced by thermoelectric voltages and electromagnetic noise. Resistance probes provide for continuous monitoring without process interruption in many fluids, except highly conductive environments such as molten metal or conductive molten salts. Prior art electrical resistance probes are described, for example, in U.S. Pat. No. 6,693,445, or U.S. Pat. No. 6,946,855.

The mass loss coupons can be made of an alloy that is the same as the structural component being monitored or can be a standard material including steels, stainless steel, copper and brass. They are inserted into the process stream for a predetermined period of time, after which they are retrieved cleaned and weighed. Mass loss coupons are considered to be reliable for measuring corrosion over longer time periods at discrete intervals. They can be used in nearly any process, but do not allow for real-time monitoring, are labor intensive and require process interruption or significant space within the process system or structure being monitored. A prior art mass coupon corrosion rate monitoring system is described in U.S. Pat. Pub. No. 201110066388.

Electrochemical methods, including Linear Polarization Resistance (LPR), Electrochemical Impedance Spectroscopy (EIS) and Electrochemical Noise (EN) are used to monitor corrosion. These measurement techniques are used to quantify kinetics of electrochemical reactions associated with corrosion. Application is limited to conductive solutions and performance is restricted in non-aqueous environments. Like resistance sensors, the resolution of electrochemical methods is reduced by thermal and electromagnetic noise. Unlike resistance and mass loss coupon methods, electrochemical techniques are unable to detect metal loss due to erosion or to provide a direct measure of cumulative material loss.

A variety of acoustic methods have been described for sensing the metal loss or formation of scale in producing hydrocarbon wells and similar environments. Several methods are based on the measuring of the measurement of transit time of the acoustic waves propagating through the fluid, structural element or both (U.S. Pat. Nos. 4,669,310; 4,872,347; 5,072,388), or on the measuring of the attenuation of acoustic energy by the structural element (U.S. Pat. Nos. 5,092,176; 5,661,233). These methods generally have poor spatial resolution and sensitivity.

More sensitive acoustic resonance methods are known. In these approaches, either piezoelectric or mechanical resonator systems are externally excited and the changes in resonance frequency of the resonator are related to the change in mass of the material removed or deposited on the resonator surface. For example, an application of an on-line quartz crystal microbalance to monitor and control the formation of organic and inorganic precipitates from hydrocarbons and water has been described in U.S. Pat. No. 5,734,098. In this approach, resonant frequency changes are measured that were related to mass loss or deposition of the resonator surface. Piezoelectric acoustic resonators, while providing high sensitivity (detection of a thickness change of the order of 1 micrometer has been reported) do not allow a user to simply differentiate between the effects caused by changes in the mass of material deposited from a liquid and changes in the properties of the liquid (temperature, pressure, density and viscosity).

A simpler mechanical resonator system that makes use of a tuning fork or similar resonator for measuring the mass loss or deposition of scale in a surface process system has been disclosed, for example in U.S. Pat. No. 5,969,235; or U.S. Pat. Nos. 7,721,605; 7,681,449; 7,866,211. A in a piezoelectric resonator, an actuator is used to excite natural vibrating frequency of the resonator. The mass loss or accumulation of scale on the tines of the tuning fork causes a shift in the natural oscillating frequency of the tuning fork as measured by exciting the force by a suitable device, such as a piezoelectric cell. Typically the frequency response for these sensors is described by theoretical relations derived for a lightly damped harmonic oscillator with single degree of freedom. For a free oscillation, or if the forcing function is sinusoidal, the resonance frequency, $f_0$, and quality factor, Q (a measure of the system damping and energy dissipation), can be represented by:

$$f_0 = (1/2\pi)\sqrt{(k/m)} \qquad \text{Equation 1}$$

$$Q = (1/c)\sqrt{(k*m)} \qquad \text{Equation 2}$$

where m=system mass, k=system stiffness, and c=velocity dependent damping. Tuning fork sensors are widely used due to low cost and the simplicity of the sensor. There are, however, several fundamental problems that impede these devices from correctly measuring the effects of mass loss and/or scale deposition.

The first of these problems occurs during operation. More specifically, the forks should be positioned inside the conduit with the sensitive to corrodible surface of the tines in normal to the flow direction, while the wall of the conduit is parallel to the flow. The rate of the physical and/or chemical processes that lead to the mass loss and/or scale deposition are therefore different for the surface of wall and for the surface of the tines, respectively.

Second, the sensor, being inserted into the flow, disturbs the flow and may form complex turbulent flow patterns between the tines thus changing the mass loss and/or scale deposition rates as compared to interaction between the wall and the undisturbed flow.

Third, the connection between the resonance frequency and mass loss is not trivial, because the mass loss or mass gain along the tines of the fork affects both system mass (m) and system stiffness (k). Moreover, there is apparent confusion in the art about this connection. For example, U.S. Pat. No. 6,928,877 and U.S. application 2006/0037399 both employ resonators and teach a relationship between the resonance frequency and mass change that is consistent with the well-known relations cited above for a single degree of freedom lightly damped mechanical oscillator: a mass decrease will result in a frequency increase and a mass increase will result in a frequency decrease. U.S. Pat. No. 7,681,449 teaches away from the prior art by discovering that mass decrease from corrosion/erosion can also result in a resonance frequency decrease. U.S. Pat. No. 7,681,449 provides evidence that the stiffness of the resonator device is also governed by the system mass, and that relationship between system mass and stiffness is location dependent: the amount of change to the system stiffness is dependent upon where the mass is lost (or gained). U.S. Pat. No. 7,681,449 shows that by selecting the proper location on the vibrating element, it is possible that the change in the stiffness to mass ratio of Equation 1 can be stiffness dominated even though mass is being lost. In that case, a loss of mass will result in a frequency decrease, teaching away from the prior art. U.S. Pat. No. 6,928,877 also teaches to make the mass additions or losses at the tip of the resonator. For U.S. Pat. No. 7,681,449, the resonator's mass change location is designed to be close to the attachment point of the tine. At this location, mass loss has a sufficient impact on system stiffness as to cause a resonance frequency decrease.

In order to resolve this apparent controversy, recent systems (such as that disclosed in U.S. Pat. No. 7,681,449) employ multiple sensors with different corrodible characteristics, measure both resonance frequency $f_o$ and quality factor Q for each sensor, and refer to the mass loss rate via a complex relationship between measured parameters in attempt to compensate the inherent trade-off between the mass and stiffness change in the tuning fork mechanical resonance method.

Furthermore, mechanical response systems installed along a conduit wall, such as U.S. Pat. Pub. 2008/0141780, disclose a method in which a change in the mechanical response of a diaphragm when actuated is used to monitor the total change in diaphragm thickness and the rate of change in thickness so as to sense the physical effects of a fluid in contact with the diaphragm. In this approach, the diaphragm can be installed flush with the conduit wall with one surface of the diaphragm exposed to the flow. However, as is the case for tuning fork sensors, the corrodible surface and elastic element in this approach are combined in one element that complicates establishing the relationship between the mechanical property of the element and the effect of the flow. For a diaphragm to be sensitive to mass loss, it must be thin and thus prone to failure due to unexpected pressure changes. In addition, diaphragm mechanical characteristics (such as resonance frequency) are affected by the fluid pressure. To compensate the fluid pressure and temperature effect, U.S. Pat. App. 2008/0141780 makes use of a second reference probe with the diaphragm impervious to the fluid. This complicates the sensor and introduces additional risk of diaphragm failure. The present invention proposes a design that is more robust and does not require a reference probe for reliable measurements of the rate of physical and chemical effects of the flow on the sensitive surface.

Moreover, U.S. Pat. No. 7,770,463 and U.S. Pat. App. Pub. 2010/0326200 disclose a sensor for measurement of the shear force exerted by fluid on a floating element installed flush with the wall. This prior art does not teach of a relation between the mass loss of the element and the mechanical resonance of the assembly that comprises the floating element. Nor does it teach what part of the total surface of the mechanical assembly should be exposed to fluid influence and which should be protected to provide a reliable relationship between the effect of interest and mass loss or gain.

There is a need for a device and method for sensing techniques that may be used for the continuous on-line detection of fluid effects on structures, that addresses present challenges and characteristics such as those discussed above.

SUMMARY

According to one embodiment of the invention, a device and method are provided where: 1) stiffness of the resonator remains constant and is not affected by the change in mass of its sensing element; 2) test flow is undisturbed; and 3) conditions are essentially identical to those occurring between the flow and the conduit wall in the absence of the probe. The device comprises a sensor including a base, or housing, adapted for fastening with a structural component and a floating member with a sensing surface that is brought in contact with the fluid. The present embodiment further includes a support member with the dual purposes of; first, mounting the floating member to the base and, second, selecting a desired value for the mechanical characteristic for a mechanical assembly. The mechanical assembly generally consists of the floating member, such as a disk or like, and the support member, such as a rod or like. The mechanical assembly will be referred to henceforth as the "cantilever". Moreover, the sensor is installed in such a way that the sensing surface of the floating member is brought in contact with the fluid, and oriented essentially parallel to the direction of the fluid flow. The cantilever is attached to the base at one end of the support member so that it can be actuated or brought to an oscillation mode by a force applied to the cantilever.

In one aspect, a change in mechanical characteristic of the cantilever, when actuated, is used to monitor total change in the floating member thickness and the rate of change in thickness with a purpose to sense the physical and/or chemical effects of a fluid in contact with the sensitive surface of the floating member. Exemplary physical and/or chemical effects caused by fluid contact that can be detected with the probes of the present invention include, for example; corrosion, erosion, scaling, and/or oxidation of the floating member surface.

The range and sensitivity of the device to the fluid effect on the sensing surface of the floating member may be tailored by the floating member geometry (thickness and surface area), material, and surface roughness selection. The mechanical properties of the cantilever are tuned by selecting the geometry (length, cross-section area) and material (density, Young's modulus) of the supporting member. Sensitivity to the physical and/or chemical effects being detected may also be achieved by selecting materials with known properties, such as corrosion or erosion properties, to use for the floating member. These materials may be the same as the structural component in which the probe is intended to be employed (e.g., a chemical process system, tank, pipeline or other) or known to have a response similar to the effect (e.g., corrosion rate) that the structural component being monitored has.

For example, if fluid corrosion is being monitored, then such corrosion causes the floating member to lose mass, which consequently alters the mechanical characteristic (e.g., resonant frequency) of the cantilever. Detection of the change in the mechanical characteristic of the cantilever when actuated (e.g., by means of the fluid shear force on the floating member) thus enables measurement of corrosion rate and cumulative corrosion damage.

The mechanical characteristic of the cantilever can be monitored using a variety of conventional sensing techniques, including optical, electrical, piezoelectric, and acoustic techniques. Preferably, the cantilever shear force response is monitored by either fiber-optic-based intrinsic optical resonance techniques such as Fiber Bragg Grating (referred below as FBG) strain gage techniques, or electrical resistive strain gage techniques.

The sensor of the present invention is applicable in a variety of open and closed systems that include chemical process systems, water pipeline systems, tanks and reactor vessels, and a broad range of piping and conduit systems that carry liquid (water, fuel, oil, etc), gas and multiphase (mixtures of liquid, gas, and solid phases) flows. Such systems include but not limited to industrial water, electric power generation, chemical, pulp and paper, heat exchanger, incinerator and fossil fuel applications. In addition, the sensors of the present invention may be employed satisfactorily to detect erosion caused, for example, by a fluid (e.g., liquid or gas) that may include particulate matter. Scaling deposits and/or high temperature oxidation caused by a fluid may also be monitored using sensing devices designed according to the present invention.

For simplicity, the physical and/or chemical effects sensor of the present invention will be referenced below as a corrosivity sensor so as to detect fluid corrosion effects. It will be understood however that this represents a presently preferred embodiment of the invention which is non-limiting with respect to the same. Further, a preferred embodiment of the sensor is based on FBG optical detection means. Similarly, another preferred embodiment of the sensors is based on Whispering Gallery Mode (WGM) optical micro-resonator detection means. Another preferred embodiment is based on semiconductor based resistive strain gage detection means. As described previously, other suitable detection means may be employed satisfactorily and thus reference to FBG, WGM and semiconductor resistive strain gage based sensors is exemplary only of presently preferred embodiments and thus non-limiting with respect to the same.

When initially placed into contact with a fluid, the sensor exhibits a first value of the mechanical characteristic. After exposure to the fluid for a predetermined period of time, the sensor exhibits a second value of the mechanical characteristic that is different from the first value of the mechanical characteristic. A change in the mechanical characteristic of the cantilever is therefore indicative of the physical effects on the sensing surface of the floating member over time caused by the fluid in contact therewith. A means for detection of the mechanical characteristic of the cantilever is operatively associated with the cantilever to measure the change in cantilever mechanical characteristics and thereby determine the physical and/or chemical effects over time of the fluid in contact with the floating member.

Thus, in the context of a corrosivity sensor, a preferred embodiment will have the floating member with one surface susceptible to corrosion placed in contact with a fluid. The other surface of the floating member, the cantilever, and any other surface of the sensor which is in contact with the fluid are protected from corrosion. The change in mechanical resonance frequency of the cantilever is monitored. Corrosion will lead to a mass loss of the floating member, thus reducing the total mass of the cantilever, m, while the stiffness, k, that is determined by the support member, will remain constant, since the fluid does not affect the support member. Therefore the mechanical resonance frequency of the cantilever will increase (see Equation 1). A means that detects the cantilever oscillation (such as a means of monitoring strain or stress of the support member in time) are operatively associated with the support member so as to measure an increase in the mechanical resonance frequency, which is indicative of the fluid corrosivity. The means of monitoring floating member strain include a FBG optical strain gage, or a semiconductor resistive strain gage, and the means of monitoring stress experienced by the floating member include a WGM optical stress gage.

The above and other objects and advantages of the present invention shall be made apparent from the accompanying drawings and the description thereof.

BRIEF DESCRIPTION OF THE DRAWINGS

The accompanying drawings, which are incorporated in and constitute a part of this specification, illustrate embodiments of the invention and, together with the general description of the invention given above, and the detailed description given below, serve to explain the principles of the invention.

DETAILED DESCRIPTION

Reference will now be made to the present embodiments of the disclosure, examples of which are illustrated in the accompanying figures. Wherever possible, the same reference numbers will be used throughout the figures to refer to the same or like parts.

Figure 1:
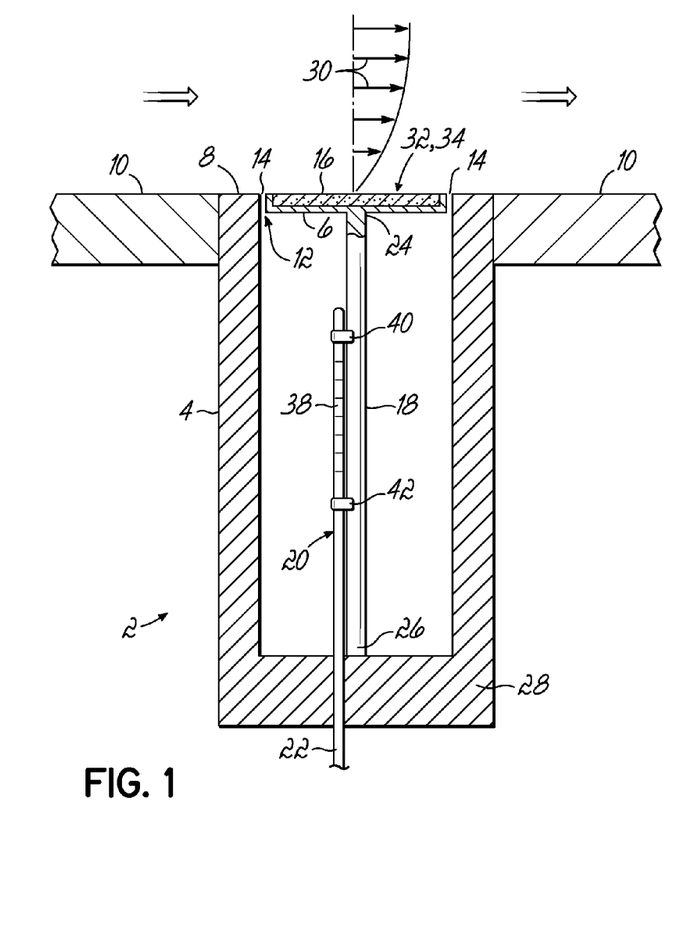
FIG. 1 is a schematic cross-sectional view of a sensor assembly positioned in a pipe wall having a Fiber Bragg Grating strain gage.

As shown in FIG. 1, a sensor or device 2, constructed in accordance with the present invention having a housing 4 and a floating member 6 at a distal end 8 of the housing 4, may be positioned through a wall 10 structural component such as a tank or pipe containing a fluid (e.g., liquid, gas, and/or multiphase) whose effects are to be monitored. As such, the floating member 6 is in contact with the fluid. The floating member 6 is positioned inside the housing 4 in such a way that it almost completely closes an opening 12 at the distal end 8 of the housing 4 allowing for a small gap 14 around the perimeter between housing 4 and floating member 6. At least an outer part 16 of floating member 6 is formed of a material that is susceptible to physical and/or chemical effects by the fluid such as corrosion.

The sensor assembly also comprises a support member 18, a means to detect the motion of the support member, such as a mechanical response sensing system 20, with a connection means 22. The sensing surface 16 of floating member 6 is mounted flush with the test section wall 10 of structural component 10. Support member 18 is firmly attached at one end 24 to floating member 6 and at a second end 26 to housing 4, at a base 28, in a manner that prevents vertical motion of the floating member 6. Therefore, the floating member 6 can move laterally for a short distance (typically of the order of ten micrometers), within gap 14 between the enclosure and the edge of the floating member 6. Since the gap 14 is much smaller than the length of the support member 18, the floating member 6 moves essentially parallel to the flow direction represented by arrows 30 and does not provide any obstacle to the flow at any position of its motion.

In addition to sensing surface 16, other surfaces of the sensor 2 may also be in contact with the fluid, including side and bottom areas of the floating member 6, inner surface of the housing 4, surface of the support member 18 and other enclosed elements such as means of detection of the mechanical characteristic. All these surfaces are made to be not susceptible to the fluid effects, therefore they are either protected by a coating or made of a material that is not susceptible to the fluid effects. When employed as a corrosivity monitor, the floating member 6 is preferably constructed from a material that corrodes at a similar rate as the material of the structural component 10, or whose damage rate correlates to the material of the structural component. Different metals can be selected for the specific structural component or process system application and fluid conditions of interest. Potential floating member 6 sensitive surface materials for the corrosivity sensors in accordance with the present invention include but are not limited to typical engineering alloys such as steel, stainless steel, copper, nickel alloys and brass. The sensitivity of the sensor 2 to the physical and/or chemical interaction such as corrosion is dictated primarily by the sensing surface and floating member 6 geometry and material properties: area, thickness, and density. Sensitivity of the sensor 2 is directly proportional to the sensitive area of the floating member 6.

Figure 1A:
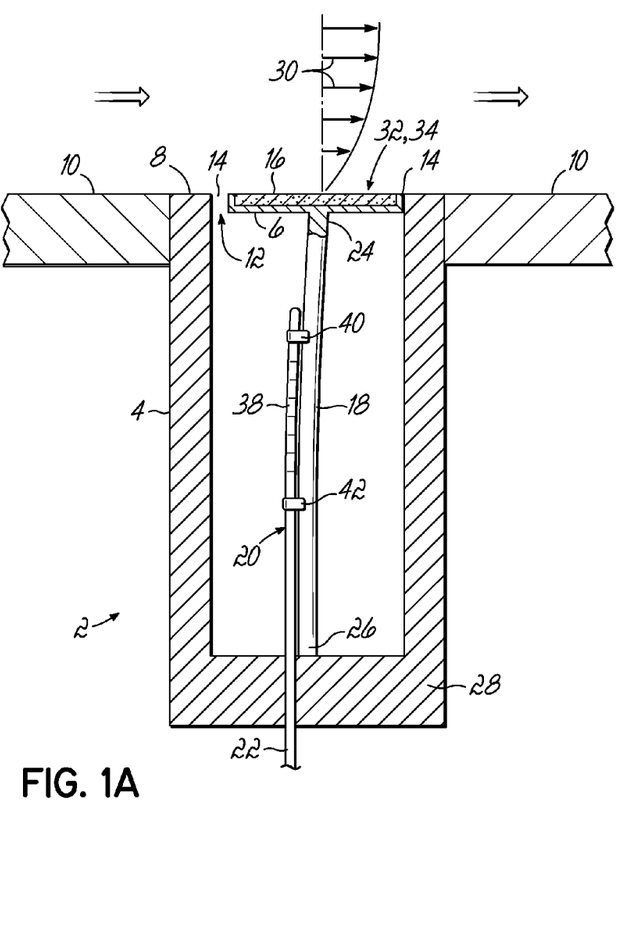
FIG. 1A is the schematic cross-sectional view of FIG. 1 depicting displacement of the floating member and deflection of the support member in the direction of flow.
Figure 1B:
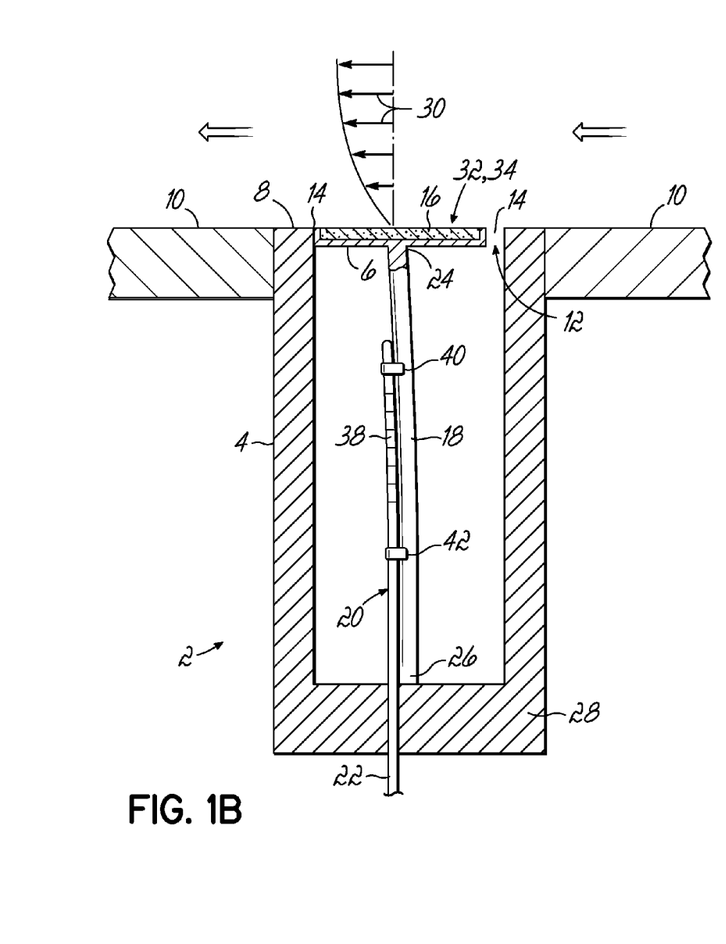
FIG. 1B is the schematic cross-sectional view of FIG. 1 depicting displacement of the floating member and deflection of the support member against the direction of flow.

The assembly of floating member 6 and support member 18 affixed to the housing 4 at second end 26 represents a mechanical oscillator 32 commonly known as a cantilever 34 beam with tip mass (referred to below as "cantilever" 34). Being initially moved away from equilibrium position (as that depicted in FIG. 1), the cantilever 34 tends to return to its equilibrium position. If the initial force action is short, such as a force caused by a short-lived disturbance in the flow, the cantilever 34 will oscillate freely around its equilibrium position between two extreme positions. FIG. 1A depicts one extreme position of the cantilever 34 in this oscillatory motion (towards the flow direction 30) and FIG. 1B depicts another extreme position of the cantilever 34 in this oscillatory motion (against the flow direction 30).

Theoretically, the natural resonance frequency of the cantilever 34 is given by Equation 1, where $$m=m_f+0.23*m_s \quad \text{Equation 3}$$

Here $m_f$ is the mass of the floating member 6, and $m_s$ is the mass of the support member 18. The effect of corrosion reduces $m_f$ and thus m, leading to increased resonance frequency of the cantilever 34.

Therefore, physical and/or chemical effects of the fluid on the floating member 6 material can be precisely monitored by measuring the natural frequency of oscillation of the cantilever 34 when the floating member 6 is exposed to the fluid flowing along the wall 10 of a structure such as pipeline or tank. Note that the stiffness of the cantilever 34 is independent from $m_f$ and thus from the effect of the fluid since the stiffness k is determined entirely by the support member 18, which is protected from the fluid, for example with a coating. This feature of the present invention allows for better connection between the measured resonant frequency of oscillation and mass loss of the floating member 6 of the sensor 2, as compared to tuning fork and membrane based sensors. In addition, since the floating member 6 is not subjected to normal force (pressure) from the fluid, its service life is higher than that of the membrane-based sensors, such as that disclosed in U.S. Pat. App. 2008/0141780, for example.

While the sensitivity of the sensor 2 to the effect of fluid is determined by the area and thickness of the floating member 6, the resolution of the sensor 2 is determined largely by the stiffness of the support member 18 that is a function of length, diameter and Young's modulus of the support member 18. The stiffness is inversely proportional to fourth power length, allowing for easy adjustment of the stiffness coefficient in sensor 2 design.

The physical effects of the fluid on the device 2 can be ascertained using one of several embodiments including (A) a passive external actuation embodiment, or (B) an active internal actuation embodiment. The active internal actuation embodiment is actuated by an actuator 36 and could include actuation by pneumatic, hydraulic, and electromagnetic means such as piezoelectric and/or solenoid actuators. A preferred embodiment is the passive external actuation of the cantilever 34 by sudden fluctuations of the shear force exerted by the flow on the sensing surface of the floating member 6.

Both active and passive actuations of the cantilever 34 result in changes in the mechanical characteristic of the cantilever 34. The mechanical characteristics that are changed by actuation include deflection and strain of the support member 18, natural resonance frequency, and the quality factor of the cantilever 34 oscillation. These mechanical characteristics can be measured using a variety of techniques such as electrical, piezoelectric, optical or acoustic approaches. A preferred embodiment of the mechanical response sensing system 20 is a fiber-optic means that includes an optical Fiber Bragg Grating strain gage (FBG) 38 being an integral part with the connection means 22, in the form of an optical fiber, that serves as optical carrier for an input and output optical signal for FBG 38. When deflected, the support member 18 strains FBG 38 that is affixed to the support member 18 at least in two places 40 and 42. The FBG 38 can be fastened mechanically or using an adhesive such as epoxy resin. In certain embodiments, FBG 38 is inserted inside the cantilever 34 body via a through bore and affixed inside. Typically the FBG 38 is pre-strained, to provide a reliable signal for deflections of the cantilever 34 both along and against the flow. Strain of FBG 38 is detected by recording the change in FBG 38 spectral characteristics using the optical fiber. The strain of FBG 38 will be periodically changing with the frequency that is equal to the frequency of oscillation of the cantilever 34.

Figure 2:
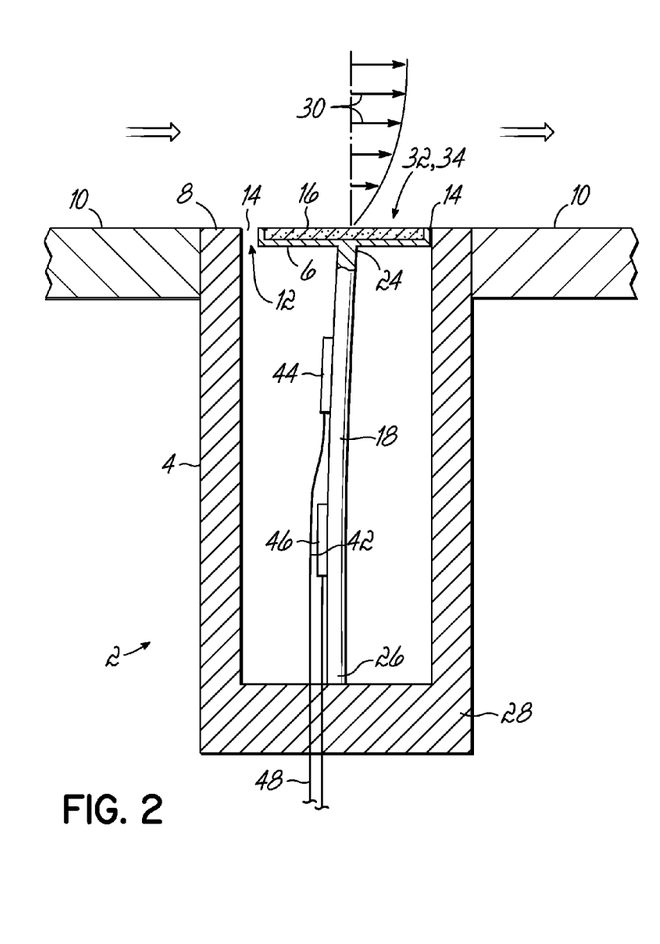
FIG. 2 is a schematic cross-sectional view of a sensor assembly positioned in a pipe wall having two resistive strain gages.
Figure 3:
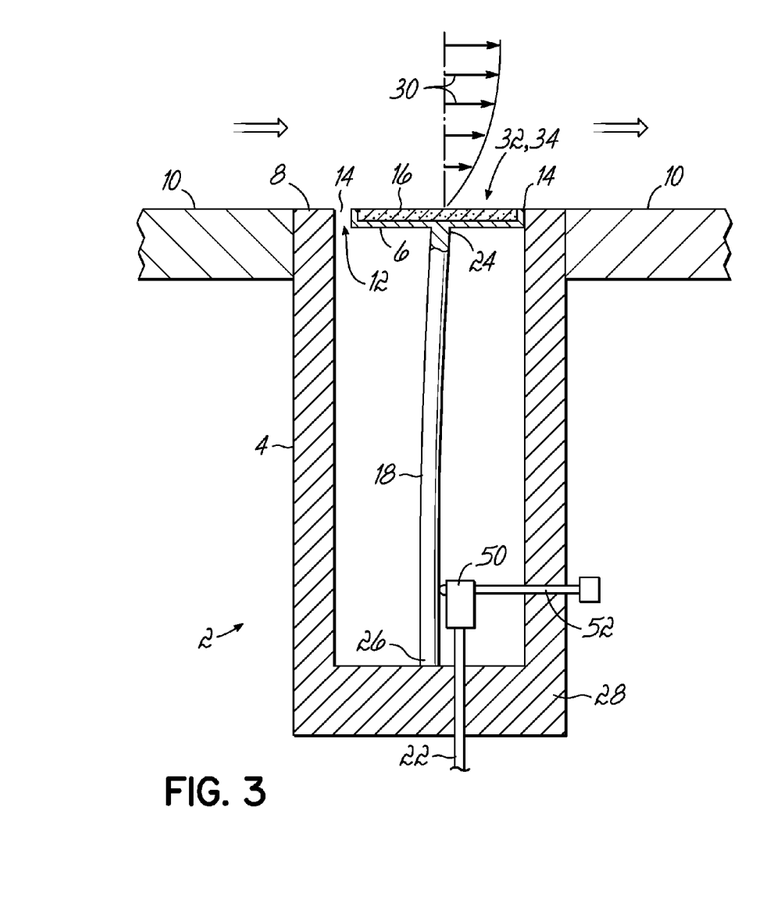
FIG. 3 is a schematic cross-sectional view of a sensor assembly positioned in a pipe wall having a Whispering Gallery Mode stress gage.

Further, another preferred embodiment is the use of resistive strain gages such as foil or a semiconductor. In FIG. 2, two strain gages 44 and 46 are affixed to support member 18 to monitor its strain with wires 48 connecting the gages to the controller. The principle of measurement for a resistive strain gage is essentially similar to that of the FBG 38 strain gage with an important difference that electric wires 48 rather than optical fibers serve as connectors between the gage and the control circuit. Another preferred embodiment uses a WGM optical microresonator load cell 50 for measurement of the stress exerted on the support member 18 by the floating member 6. In FIG. 3, the WGM optical load cell 50 is tightly positioned between the housing 4 and the support member 18 using the adjustment screw 52 typically near the second end 26 as a point of attachment for support member 18 to housing 4 so the force applied to floating member 6 is transferred to load cell 50 by support member 18. Load cell 50 is connected to the optical controller via connection means 22 as an optical fiber. The WGM optical load cell 50 is capable to detect deflections of the support member 18 of a fraction of a nanometer, but it yields to FBG 38 strain gages in robustness.

Figure 4:
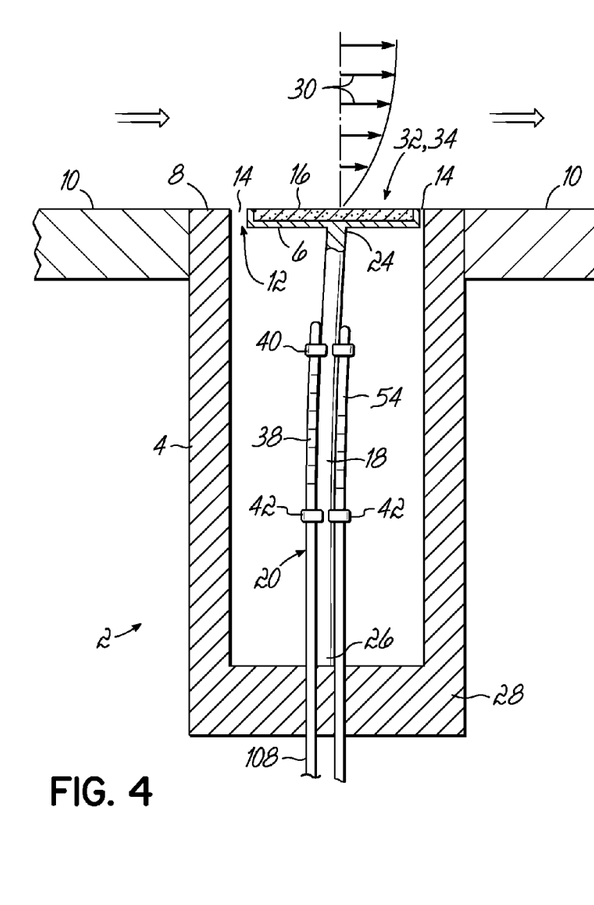
FIG. 4 is a schematic cross-sectional view of a sensor assembly positioned in a pipe wall having two strain gages.

FIG. 4 represents another preferred embodiment of a sensor 2 constructed according to the present invention. Two optical strain gages FBG1 38 and FBG2 54 are attached to the opposite sides of the support member 18. This arrangement allows for compensation of temperature fluctuations that may affect the gages. While the support member 18 is deflected along the flow, stretching of FBG1 38 is increased as compared to its initial pre-stretched condition, while stretching of FBG2 54 is decreased compared to its initial pre-stretched condition; therefore, by recording the differential signal between FBG1 38 and FBG2 54, it is possible to exclude the environmental factor, such as fluid temperature change, that affects both FBG1 38 and FBG2 54 in similar way.

Figure 4A:
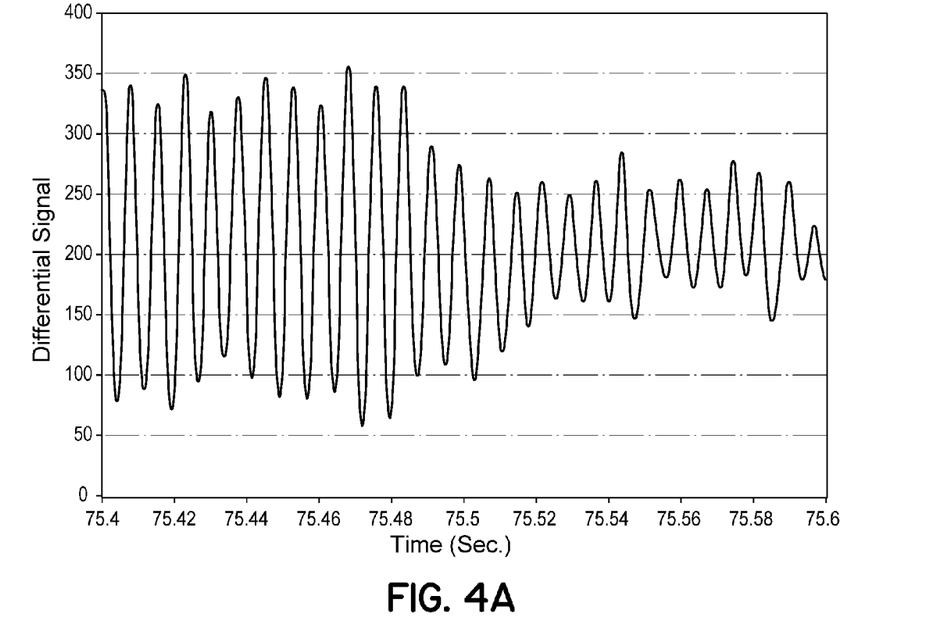
FIG. 4A is a plotted graph of the differential signal with respect to time for compensating temperature effects according to the schematic of FIG. 4.
Figure 4B:
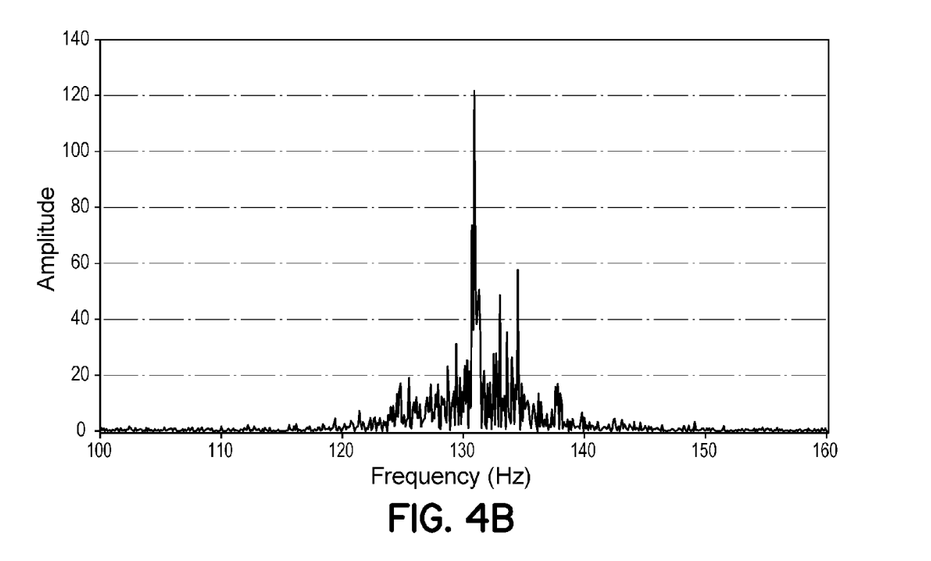
FIG. 4B is a plotted graph of the amplitude with respect to signal frequency for compensating temperature effects according to the schematic of FIG. 4.
Figure 4C:
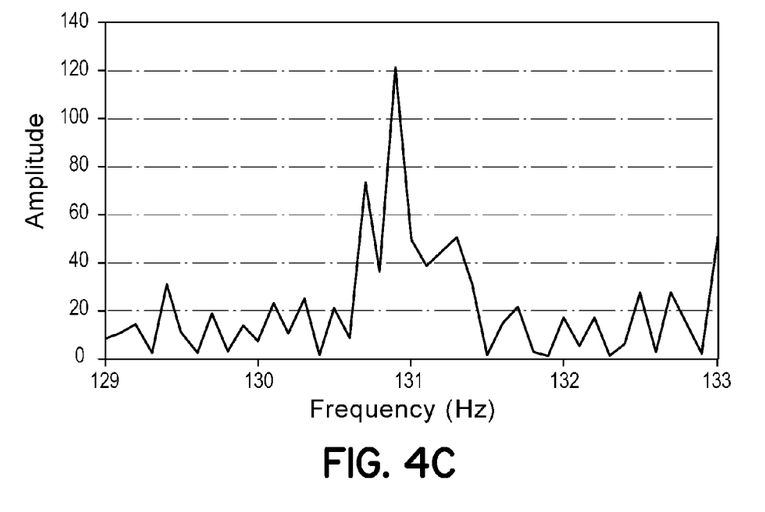
FIG. 4C is a plotted graph of the amplitude with respect to signal frequency for compensating temperature effects according to the schematic of FIG. 4.
Figure 4D:
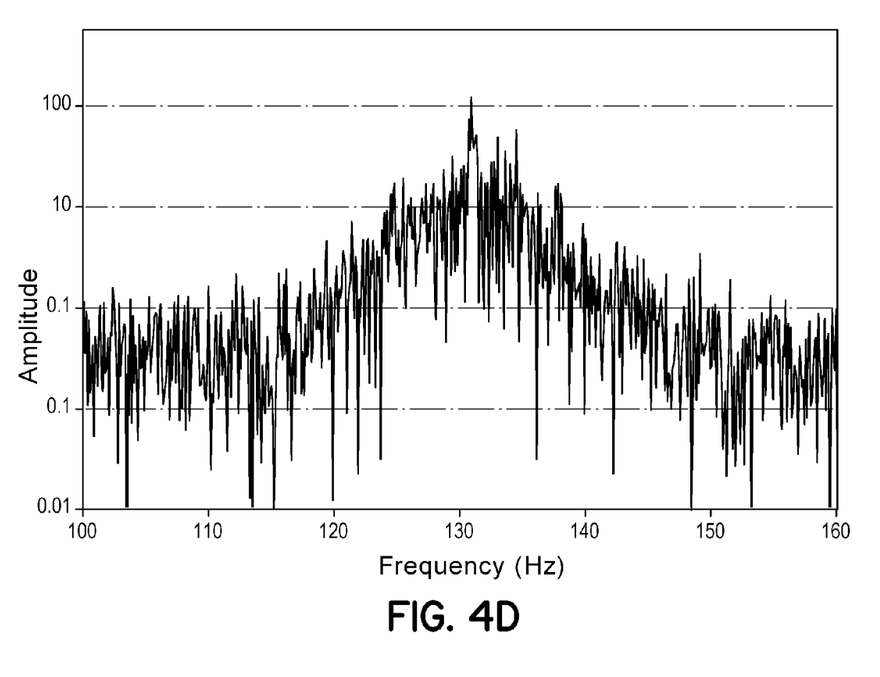
FIG. 4D is a plotted graph of the amplitude with respect to signal frequency for compensating temperature effects according to the schematic of FIG. 4.

FIG. 4A represents an exemplary signal recorded in the flow of turbulent water using a sensor 2 constructed in accordance with the concept illustrated by FIG. 4. The plot depicts the dependence of voltage that is proportional to the difference in strains measured by FBG1 38 and FBG2 54, on time. FIG. 4B represents the Fourier transformation, or frequency spectrum of the signal of FIG. 4A. The fundamental resonance frequency corresponds to the frequency at the largest amplitude. A benefit of the natural frequency based sensing method is that measurement of the applied excitation force amplitude is not required. Nor is an absolute measure of the amplitude response, since the physical effect measurement is based on resonance frequency.

In an exemplary measurement illustrated by FIGS. 4, 4A, and 4B, a frequency shift of 0.2 Hz can be recorded in 10 seconds of data accumulation. Using Equations 1 and 3 and assuming that $m_f \approx 0.23 \cdot m_s$, $$\Delta m/m_f \approx 4 \Delta f_0 / f_0 \qquad \text{Equation 4}$$

For the measurement of FIGS. 4, 4A, and 4B, this lead to a detection limit of 0.6%.

Another mechanical characteristic that could be assessed from the measurement of cantilever's 34 oscillation signal such as shown in FIG. 4A is the quality factor, Q, which is the measure of mechanical energy dissipation. Q may be estimated by $$Q = f_o / \delta f \qquad \text{Equation 5}$$

where $f_o$ is the resonance frequency and $\delta f$ is the width of the resonance peak at the half height.

Figure 5:
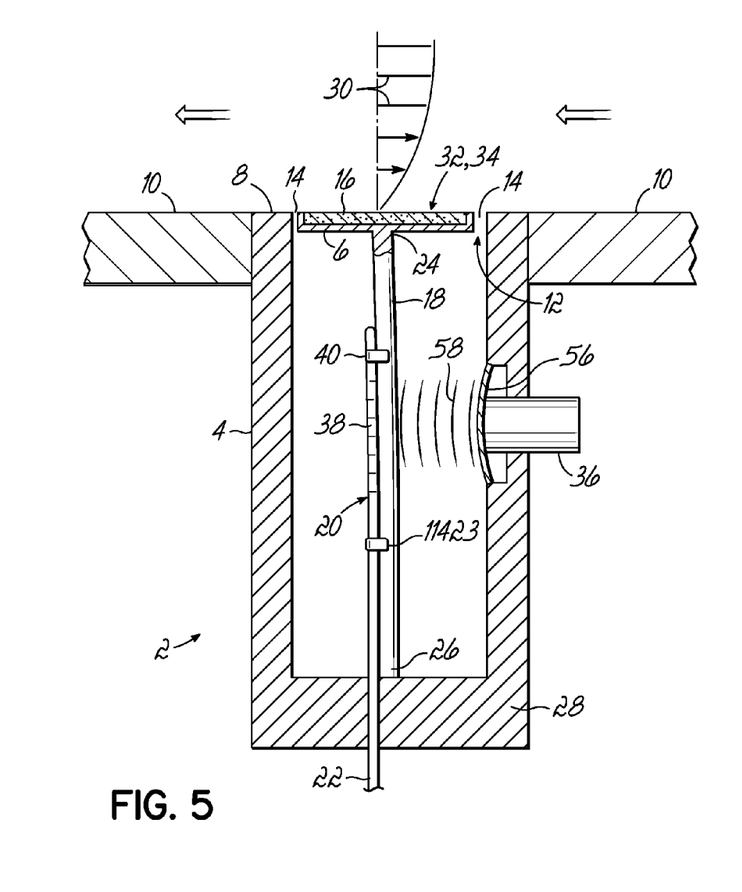
FIG. 5 is a schematic cross-sectional view of a sensor assembly positioned in a pipe wall having active internal actuation.

In the embodiments of FIGS. 1, 2, 3, and 4, passive actuation was used. Free oscillations of the cantilever 34 are observed and measured, which were actuated by sudden fluctuations of the shear force exerted by the fluid on the floating member 6 sensing surface. The natural frequency can also be determined by applying a sinusoidal excitation to the cantilever 34 over a range of frequencies while observing the magnitude and phase of the response at each frequency. This approach of internal actuation makes use of forced oscillation of the cantilever 34. For internal actuation, a piezoelectric force actuator 36 paired with an FBG 38 strain gage is one embodiment that can be used to apply a sinesweep measurement to determine the natural frequency of the cantilever 34. The actuator 36 applies the sinusoidal excitation force to a diaphragm 56 that may be directly connected mechanically to the support member 18, or, as shown in FIG. 5, is installed flush with the surface of the enclosure on a distance from the support member 18 surface. In this embodiment, the actuator 36 oscillates diaphragm 56 that provides a hydraulic action illustrated by sound waves 58 to support member 18 by applying a periodic force through the fluid that fills the inside of the sensor body. The cantilever 34 oscillates with the frequency of the actuator 36, and the support member 18 strain response is detected with the FBG 38 strain gage. The actuator 36 frequency that provides the maximum amplitude response is the measure of the natural frequency of the cantilever 34.

The preferred embodiment of a corrosivity sensor is actuated by the flow shear force in the pipeline without need for further mechanisms.

The accuracy of the fluid effect sensor 2 can be further improved by the use of a reference sensor (not shown). The reference and fluid effect sensors are located in close proximity to each other such that they are subject to similar fluid conditions. The reference sensor (not shown) is used to remove other environmental effects such as temperature to obtain a precise measurement of the mechanical characteristic that can be used to quantify the mass change and therefore corrosion, erosion, or scaling of the floating member 6. By comparing the fluid effect sensor 2 and reference sensor (not shown) response to actuation such as flow turbulences, the mass change of the floating member 6 in the fluid effect sensor 2 may be calculated using an appropriate theoretical model.

In one embodiment, the reference sensor (not shown) could be provided by a commercially available probe such as a temperature probe placed near the corrosivity sensor in the process stream. A preferred embodiment of the reference sensor (not shown) of the present invention is a sensor constructed essentially identical to the fluid effect sensor 2, except that the sensing surface of the floating member 6, as all other parts of the sensor, is protected from the fluid. In this embodiment, protection is accomplished by coating or covering the floating member 6 with a material that produces a barrier to the fluid. The barrier is thin and does not substantially alter the mechanical characteristics of the reference sensor (not shown). Barrier materials may be coatings or sleeves or covering of organic and polymeric materials, such as a polyurethane, epoxy, or fluorocarbon. In another preferred embodiment, the reference floating member 60 is made of a more inert material than the corrosivity sensor. The inert material is chosen for resistance to the fluid effects and may include non-metals such as glass or ceramics and metals and alloys such as steels, stainless steels, brass, copper, aluminum alloys, and nickel based alloys.

Extraneous environmental effects, such as temperature affect both the reference and corrosivity sensors in the same manner. Comparing the response of the reference and corrosivity sensors therefore provides a measurement of the physical effects such as corrosion while being robust to other extraneous environmental factors. This additional thermal compensation may be a benefit for measurement precision.

Another embodiment of the present invention is an active, internally actuated fluid effect sensor 2. The actuated physical effects sensor 2 uses a built-in means for actuating the cantilever 34. The active internal actuation embodiment would include actuation by pneumatic, hydraulic, and electromagnetic means such piezoelectric and/or solenoid actuators. A preferred embodiment of active internal actuation technique is the application of fluid pressure to the side of the support member 18. Another preferred embodiment is the actuation of the support member 18 directly from the side using a device such as a piezoceramic actuator 36 or solenoid.

The internally actuated sensor 2 utilizes the same cantilever 34 mechanical characteristic measurement strategies as the passive externally actuated fluid effect sensor 2 (i.e. optical or resistive strain gage). The sensor's mechanical characteristic is determined by measuring the cantilever 34 response to the applied actuation. One benefit of this embodiment of the fluid effect sensor 2 is that the internally actuated sensor 2 of the present invention could be used in a broader range of applications including still fluids, since no shear force from the fluid is required for sensor actuation and function.

Figure 6:
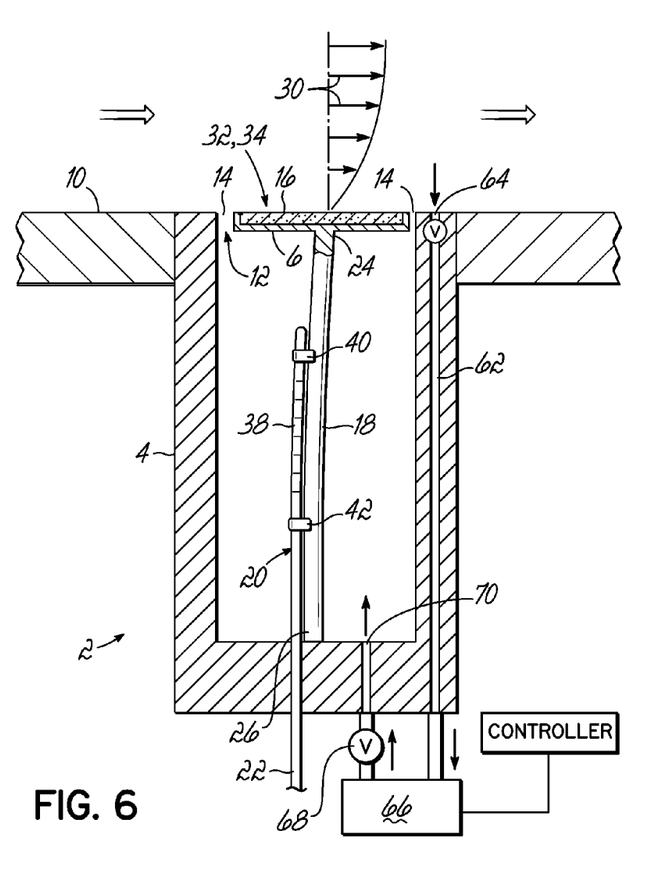
FIG. 6 is a schematic cross-sectional view of a sensor assembly positioned in a pipe wall having a purging system.

To avoid the accumulation of particulate matter inside the fluid effect sensor 2, a purging system can be used. Purging of the device 2 may be done with either the same fluid it is in contact with, ambient air, or with a separate supply of gas or liquid. One possible embodiment of a fluid effect sensor 2 is demonstrated in FIG. 6. Inlet channel 62, constructed inside sensor housing 4, has an inlet 64 so that downflow from the floating member 6 lets microcompressor 66 purge a controlled amount of fluid into the bottom part of the sensor 2 through output valve 68 and outlet 70. Microcompressor 66 can be activated periodically following a predetermined schedule or as a reaction to an unexpected sudden change in the sensor 2 response.

While the present invention has been illustrated by the description of one or more embodiments thereof, and while the embodiments have been described in considerable detail, they are not intended to restrict or in any way limit the scope of the appended claims to such detail. The various features shown and discussed herein may be used alone or in combination. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope or spirit of Applicants' general inventive concept.

What is claimed is:

1. A device for measuring an interaction effect between a fluid and a wall of a structural component containing the fluid, the device comprising;
   a mechanical oscillator, including:
      a floating member at least partially formed from a first material configured to be corrosively susceptible to at least one of either physical or chemical effects of the fluid; and
      a support member formed from a second material resistant to said at least one of either physical or chemical effects of the fluid,
      wherein said floating member is mounted to said support member and have a combined mechanical characteristic;
      a housing, said mechanical oscillator being affixed within said housing, said housing being adaptably fastened to the structural component such that said floating member is in contact with the fluid;
   a mechanical response sensing system configured to measure said mechanical characteristic,
   wherein measurements of said mechanical characteristic are configured to be indicative of the measurements of the interaction effect between the fluid and the wall; and
   wherein said floating member has a mass and said support member has a spring constant, said mass configured to reduce as a physical or chemical effect of the fluid and said spring constant configured to remain unchanged.

2. The device of claim 1 wherein said housing has a distal end and further comprises:
   an opening at said distal end of said housing, said opening being through the wall of the structural component; and
   a base, said base being opposite said distal end.

3. The device of claim 2 wherein said floating member is positioned within said opening and flush with the wall of the structural component along a direction of fluid flow, said support member being affixed to said base such that said floating member is not subjected to motion in a normal direction of fluid flow.

4. The device of claim 2 wherein said floating member is positioned within said opening and flush with the wall of the structural component along a direction of fluid flow, said floating member and the wall defining a gap surrounding at least a portion of said floating member.

5. The device of claim 4 wherein said floating member of said mechanical oscillator is configured to be movable within said gap essentially parallel to the direction of fluid flow.

6. The device of claim 5 wherein said mechanical response sensing system is operably connected to said support member to measure said mechanical characteristic.

7. The device of claim 1 wherein said housing further comprises a base, said floating member cantilevered from said base.

8. The device of claim 1 wherein said mechanical response sensing system is at least one of either a Fiber Bragg Grating gage, a Whispering Gallery Mode Optical gage, or an electrical resistive strain gage.

9. The device of claim 1 wherein said mechanical characteristic is at least one of either displacement of said floating member, deflection of support member, resonant frequency of said mechanical oscillator, and quality factor of said mechanical oscillator.

10. The device of claim 1 wherein said floating member is a metal or a metal alloy material.

11. The device of claim 1 wherein said floating member is formed from a material configured to correlate to the physical or chemical effects of the fluid contacting the wall.

12. The device of claim 11 wherein said floating member is formed from the same material as the wall of the structural component containing the fluid.

13. The device of claim 1 further including an actuator for active actuation, said actuator configured to actively generate said mechanical characteristic measured by said mechanical response sensing system.

14. The device of claim 1 further including a reference sensor configured to measure a temperature of the fluid.

15. The device of claim 1 having a plurality of said mechanical response sensing systems configured to compensate for changes in a fluid temperature that affect said mechanical characteristic.

16. The device of claim 1 further including:
   an inlet channel having an inlet and an outlet, said outlet positioned adjacent to a flow of fluid and said inlet positioned within said housing,
   wherein the fluid is configured to flow from said inlet and into said housing to operatively purge the device free of a removable particulate matter.

17. A method of measuring an interaction effect between a fluid and a wall of a structural component containing the fluid with a mechanical oscillator having a floating member and a support member, the method comprising;
   directing the fluid along the floating member,
   oscillating the mechanical oscillator;
   measuring a first value of a mechanical characteristic of the mechanical oscillator while oscillating;
   contacting the fluid to the floating member formed from a first material;
   altering a mass of said floating member and maintaining a spring constant of the support member;
   protecting the support member formed from a second material from both a physical and chemical effect; and
   measuring a second value of the mechanical characteristic after a predetermined period of time after contacting the fluid to the floating member.

18. The method of claim 17 further comprising:
   comparing the first value to the second value; and
   correlating the comparison of the first value and the second value to the interaction effect between the fluid and the wall of the structural component containing the fluid.

19. The method of claim 17 further comprising:
   decreasing the mass of the floating member; and
   maintaining a spring constant of the support member.

20. The method of claim 17 further comprising:
   actively oscillating the mechanical oscillator with an actuator.

21. The method of claim 17 wherein the first and second value of the mechanical characteristic is measured by at least one of either a Fiber Bragg Grating gage, Whispering Gallery Mode Optical gage, or an electrical resistive strain gage.

22. The method of claim 17 wherein the mechanical characteristic measured is at least one of deflection of the support member, strain of the support member, resonant frequency of the mechanical oscillator, and quality factor of the mechanical oscillator.

23. The method of claim 17 further including:
   exerting shear force on the mechanical oscillator.

24. The method of claim 17 further including:
   purging particulate matter away from the mechanical oscillator.

* * * * *